United States Patent [19]
Kohama

[11] Patent Number: 5,689,183
[45] Date of Patent: Nov. 18, 1997

[54] ELECTROMAGNETIC-INDUCTION TYPE INSPECTION DEVICE EMPLOYING TWO INDUCTION COILS CONNECTED IN OPPOSITE PHASE RELATION

[75] Inventor: Hiroaki Kohama, Tokyo, Japan

[73] Assignee: Kaisei Engineer Co., Ltd., Tokyo, Japan

[21] Appl. No.: 513,626

[22] Filed: Aug. 10, 1995

[30] Foreign Application Priority Data

Aug. 11, 1994 [JP] Japan ................. 6-189306

[51] Int. Cl.$^6$ .................. G01N 27/90; G01R 33/12
[52] U.S. Cl. ............... 324/233; 324/225; 324/232; 324/241
[58] Field of Search ................. 324/225, 227, 324/229, 230, 232, 233, 239–243, 329

[56] References Cited

U.S. PATENT DOCUMENTS

| | | | |
|---|---|---|---|
| 3,478,263 | 11/1969 | Hentschel | 324/233 |
| 3,823,368 | 7/1974 | Mansson et al. | 324/233 |
| 3,916,301 | 10/1975 | Vild et al. | 324/233 X |
| 4,059,795 | 11/1977 | Mordwinkin | 324/233 |
| 4,063,230 | 12/1977 | Purinton et al. | 324/233 X |
| 4,086,527 | 4/1978 | Cadot | 324/233 |
| 4,594,549 | 6/1986 | Smith et al. | 324/232 |
| 4,799,010 | 1/1989 | Muller | 324/240 |
| 4,881,031 | 11/1989 | Pfisterer et al. | 324/233 |
| 4,954,777 | 9/1990 | Klopfer et al. | 324/241 X |

FOREIGN PATENT DOCUMENTS 1403734  8/1975  United Kingdom ............ 324/241

*Primary Examiner*—Gerard R. Strecker
*Attorney, Agent, or Firm*—Wenderoth, Lind & Ponack

[57] ABSTRACT

An electromagnetic-induction type inspection device for inspecting a test specimen by placing the specimen in electromagnetic fields produced by exciting coils, detecting induction currents from induction coils set in the electromagnetic fields, and analyzing a composite signal composed of the amplitude and phase components contained in a differential current between the induction currents. The composite signal is expressed as a waveform which is displayed on a display unit, so that deformed portions of the waveform, which represent internal defects or other abnormalities in the specimen, can be identified.

6 Claims, 6 Drawing Sheets

5,689,183

ELECTROMAGNETIC-INDUCTION TYPE INSPECTION DEVICE EMPLOYING TWO INDUCTION COILS CONNECTED IN OPPOSITE PHASE RELATION

BACKGROUND OF THE INVENTION

1. Field of the Invention

This invention relates to an electromagnetic-induction type inspection device, and more particularly to a device for inspecting the conditions such as internal defects of a specimen by measuring a change of electromagnetic induction caused by placing the specimen in an electromagnetic field.

2. Description of the Prior Art

There have been so far known electromagnetic-induction type inspection devices in which an electromagnetic induction current induced in an electromagnetic field is measured for inspecting a conductive test specimen. As the conductive specimen generates an eddy current in the electromagnetic field, the induction current induced by the electromagnetic field changes. Thus, by measuring the change of induction current, the conditions such as the material, defects and dimensions of the specimen can be recognized. These inspection devices have been used widely.

As shown in FIG. 1 as one example, the conventional electromagnetic-induction type inspection device generally comprises an oscillator 1 for generating an alternating current, a sensor 2 having an exciting coil 2a for producing an electromagnetic field F with the application of the alternating current and an induction coil 2b in which an induction current is induced by the electromagnetic field F, a balance circuit 3 such as a bridge circuit for detecting changes of induction current, an amplifier 4 for amplifying a signal representing the change of induction current, a synchronous detector 5 for detecting a signal having a specific phase angle, a phase shifter 6 for adjusting a difference in phase between the exciting coil 2a and the induction coil 2b, and a display 7 such as an oscilloscope, measuring instructions and data recorder.

When a conductive test specimen S is placed in the electromagnetic field F produced by applying the alternating current from the oscillator 1 to the exciting coil 2a of the sensor 2, an eddy current is generated by the conductive specimen S and detected by the induction coil 2b. As the result of generating the eddy current, the induction current induced within the induction coil 2b changes. The changes in induction current are detected by the balance circuit 3 to issue an electric potential signal representing the changes of induction current. The electric potential signal is amplified by the amplifier 4 and fed to the synchronous detector 5. At the same time, a phase signal having a specific phase which is determined to eliminate noise by the phase shifter 6 is given to the synchronous detector 5. Consequently, information signals showing the conditions such as defects, quality of material and dimensions of the specimen are derived by the synchronous detector 5 and fed to the display 7.

The eddy current generated by the specimen S mostly flows along the surface of the specimen and decreases as the depth advances. Therefore, the inspection device of this type is suitable to detect merely surface defects and dimensions of the specimen. However, the conventional inspection device entails problems such as difficulty in detecting internal defects particularly at a depth in the test specimen and cannot provide accurate inspection performance.

OBJECT OF THE INVENTION

This invention was made to eliminate the drawbacks suffered by the conventional inspection device and has an object to provide an electromagnetic-induction type inspection device capable of inspecting the conditions such as defects, material and dimensions of a given test specimen and detecting not only surface defects but also internal defects in the specimen with a very high accuracy.

Another object of this invention is to provide an electromagnetic-induction type inspection device capable of achieving high accuracy in the inspection of the test specimen regardless of the quality of material, magnetic permeability, surface conditions and physical dimensions of the specimen, and the testing speed and testing arrangement.

Still another object of this invention is to provide an electromagnetic-induction type inspection device capable of readily determining the location of various forms of defects in the given specimen.

Yet another object of this invention is to provide an electromagnetic-induction type inspection device capable of increasing the sensitivity to an alternating electromagnetic field while eliminating disturbance noises.

A further object of this invention is to provide an electromagnetic-induction type inspection device capable of measuring magnetic permeability according to the phase of an induction current derivable from an induction coil and specific resistance according to the amplitude of the induction current.

SUMMARY OF THE INVENTION

To accomplish the objects described above according to this invention, there is provided an electromagnetic-induction type inspection device comprising an oscillator for generating an alternating current, an electromagnetic induction sensor unit having exciting coils for producing electromagnetic fields and induction coils for having induction currents induced therein, which induction coils are connected in opposite phase relationship so as to permit the induced induction currents to cancel each other for outputting a differential current between the induction currents, and a signal processor for detecting the phase and amplitude of the differential current from the sensor unit to output a composite signal composed of the phase and amplitude of the differential current.

The signal processor includes an amplitude detector for detecting the amplitude of the differential current, a phase detector for detecting the phase of the differential current, and a circuit for synthesizing the amplitude and phase signals outputted from the amplitude and phase detectors to produce a composite signal.

The phase and amplitude of the differential current vary with not only the frequency of the alternating current applied to the exciting current, but also with various conditions of a conductive specimen placed in the electromagnetic field generated by the exciting coils. By analyzing the composite signal of the phase and amplitude of the differential current, the conditions such as internal defects in the conductive specimen can be recognized accurately.

The composite signal is given in a waveform and displayed on a display unit to facilitate the analysis of the conditions of the specimen.

Other and further objects of this invention will become obvious upon an understanding of the illustrative embodiments about to be described, and various advantages not referred to herein will occur to one skilled in the art upon employment of the invention in practice.

DESCRIPTION OF THE PREFERRED EMBODIMENTS

The inspection device according to this invention may be categorized as an eddy current electromagnetic-induction type of device, in which the intensity of an electromagnetic field is measured in the form of amplitude equivalent to impedance, and noise is eliminated by adjusting the phase of an induction current. To be specific, the change of electromagnetic field is measured by the permeability (phase) and impedance (amplitude) of an electric conductor. The permeability may correspond to the amplitude of the induction current and the impedance may correspond to the phase of the same. According to the Maxwell field equations; when a conductive object is placed in an electromagnetic field, three kinds of electric signals indicating solid state properties (specific resistance, magnetic permeability, and dielectric constant) of the object can be obtained. In particular, in order to obtain the electric signals representing the specific resistance and magnetic permeability, it is necessary to adjust the frequency of the exciting current for producing the electromagnetic field and measure the amplitude and phase of the induction current.

Since static magnetic flux and alternating magnetic flux penetrate conductive materials such as metal, the conditions and properties of a conductive specimen placed in the electromagnetic field generated by an alternating current can be recognized by measuring the change of intensity of the electromagnetic field. The present invention makes use of, in addition to such electrical properties, a phenomenon in which the alternating magnetic flux depends on the frequency of the alternating current that is applied to produce the electromagnetic field. That is, the frequency of the alternating current for producing the electromagnetic field is adjusted in the present invention.

To be more specific, the first embodiment of this invention comprises forming alternating electromagnetic fields having equal magnetic force with an alternating current having adjusted frequency, placing a conductive test specimen in one of the electromagnetic fields, measuring an induction current or induction voltage induced electromagnetically by the electromagnetic fields to obtain an electric signal representing the intensity change caused by placing the test specimen in the electromagnetic field, and identifying the magnetic permeability and specific resistance of the specimen from the electric signal. The resultant data obtained as the result of finding the magnetic permeability and specific resistance are displayed.

Figure 1:
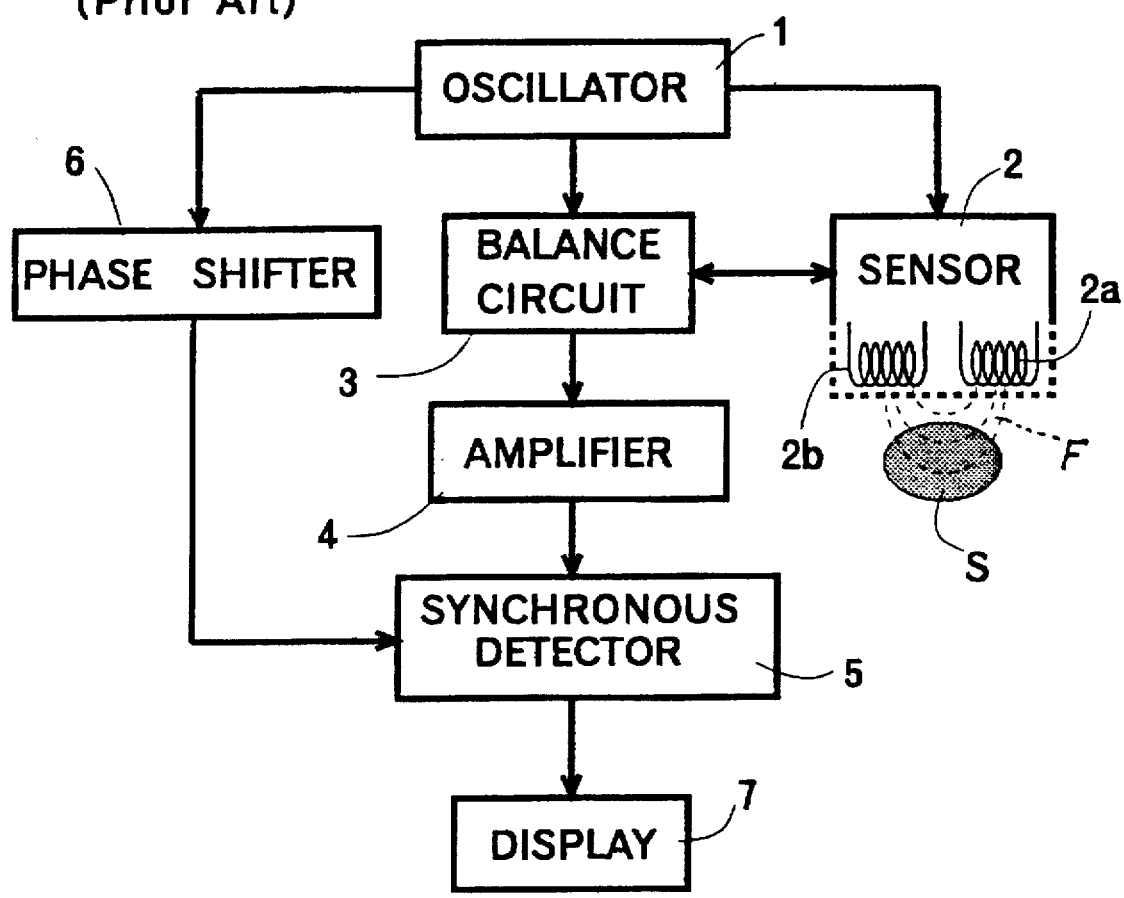
FIG. 1 is a block diagram showing a conventional electromagnetic-induction type inspection device.
Figure 2:
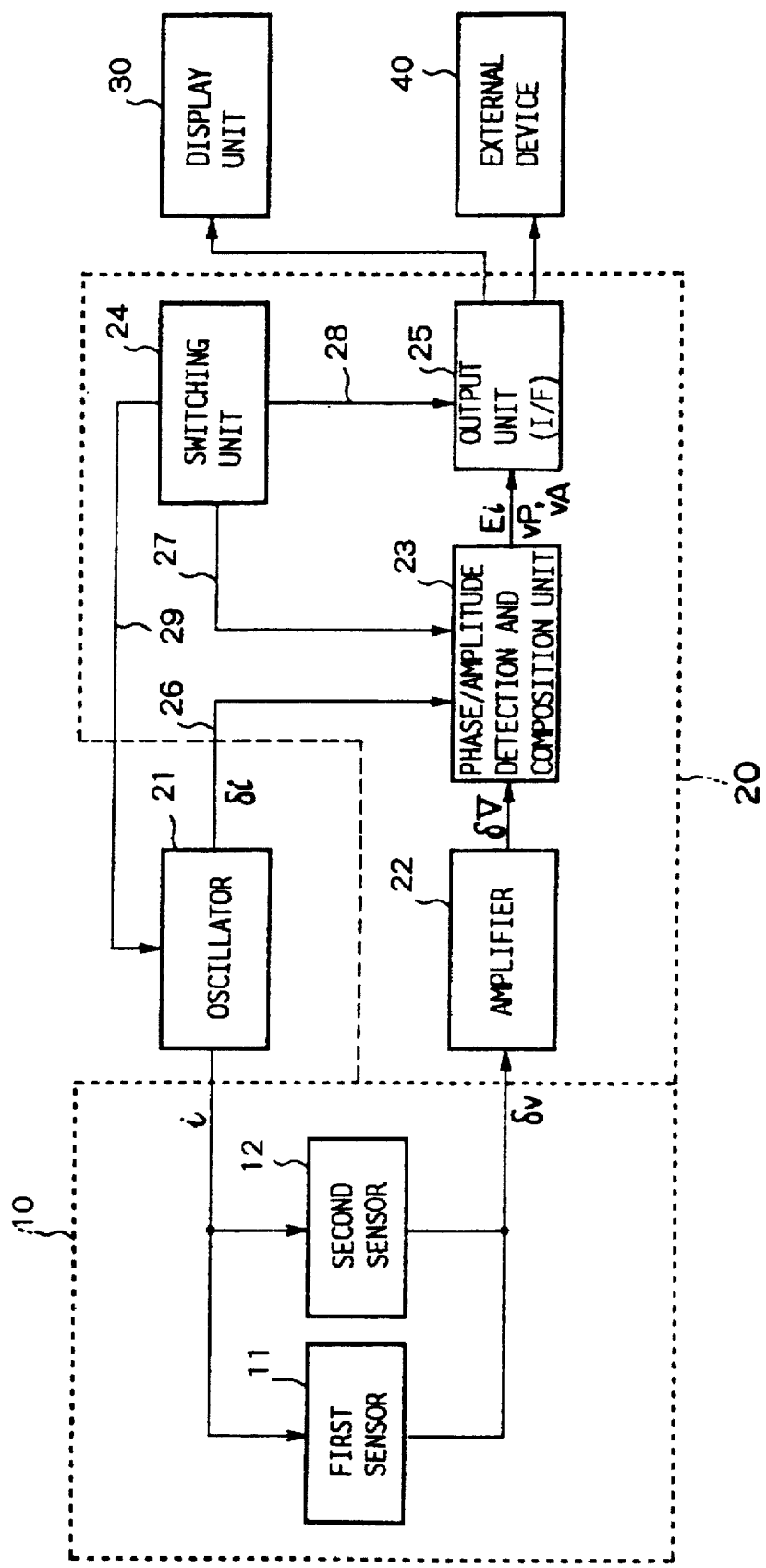
FIG. 2 is a block diagram showing one embodiment of an electromagnetic-induction type inspection device according to this invention.

To put it concretely, as illustrated in FIG. 2, the electromagnetic-induction type inspection device according to this invention comprises an electromagnetic induction sensor unit 10 for detecting the induction current or induction voltage induced electromagnetically to issue an induction signal, a signal processor 20 for detecting the phase and amplitude of the induction signal fed from the sensor unit 10 to obtain a composite signal composed of the phase and amplitude of the induction signal, a display unit 30 for displaying the phase and amplitude indicating the properties of the conductive specimen, and an external device 40 in which data such as the phase and amplitude of the induction signal from the signal processor 20 are processed and stored in a magnetic recording medium such as a magnetic recording tape, magnetic recording disk and MO disk.

Figure 3A:
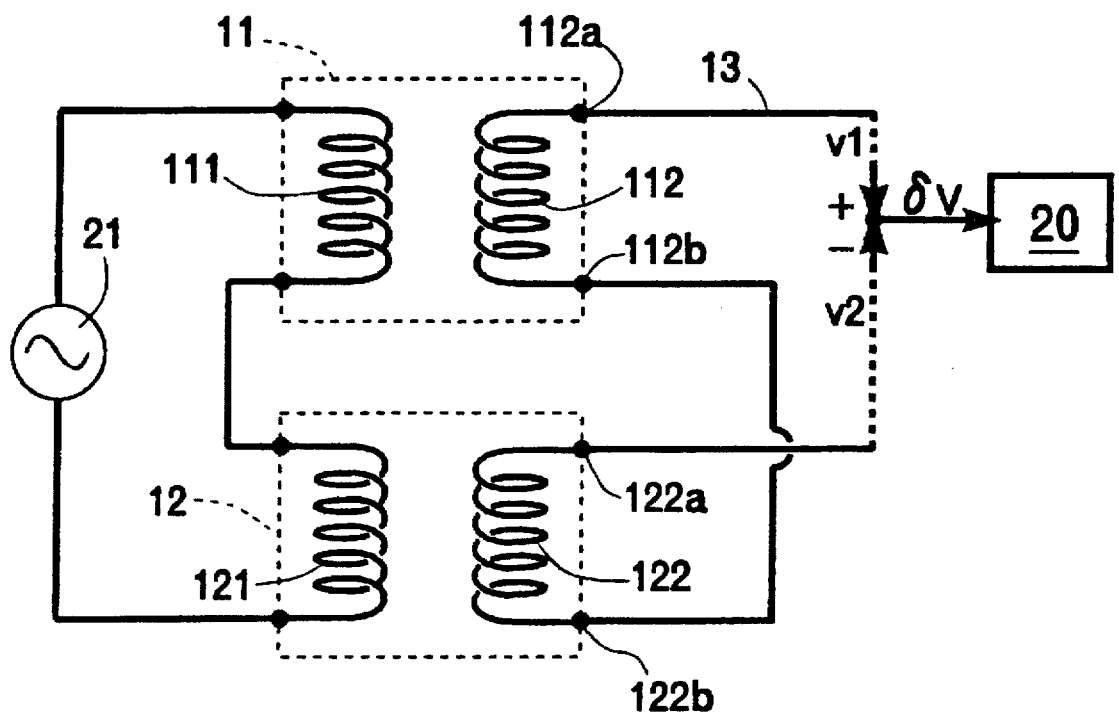
FIG. 3A is a schematic circuit diagram of a sensor unit in the inspection device of this invention.
Figure 3B:
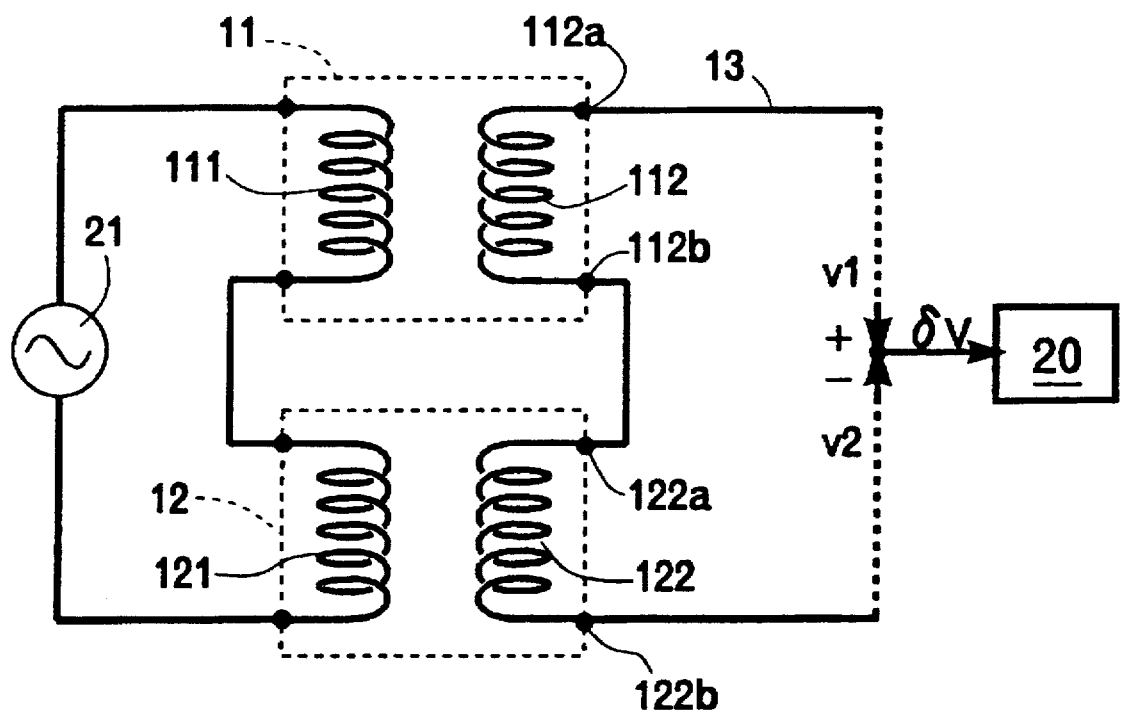
FIG. 3B is a schematic circuit diagram of a modified form of the sensor unit in the inspection device of this invention.

The aforementioned sensor unit 10 comprises a first sensor 11 and a second sensor 12. As shown in FIG. 3A and FIG. 3B, the first sensor 11 has an exciting coil 111 for forming an alternating electromagnetic field with the application of an alternating current, and an induction coil 112 having an induction current v1 that is proportional to the intensity of the electromagnetic field produced by the exciting coil 111. The second sensor 12 has an exciting coil 121 and an induction coil 122 which are similar in structure and function to the exciting and induction coils in the first sensor 11 so as to induce an induction current v2.

The induction coils 112 and 122 are connected in opposite phase relationship as shown in FIG. 3A. That is, since the induction coils 112 and 122 are wound in the same direction, the front terminals 112a and 122a of the coils 112 and 122 are connected to the signal processor 20, and the rear terminals 112b and 122b are connected to each other as illustrated. Therefore, the induction currents v1 and v2 output from the induction coils 112 and 122 connected in opposite phase relationship are essentially subjected to subtraction as equivalently indicated by the dotted arrows in FIG. 3A, consequently producing a differential current δv.

On the contrary, in the case where the induction coils 112 and 122 are wound in the opposite directions to each other as shown in FIG. 3B, they may be arranged so as to connect the front terminal 112a of the first coil 112 and the rear terminal 122b of the second coil 122 to the signal processor 20, and connect the rear terminal 112b of the first coil 112 and the front terminal 122a of the second coil 122 to each other as illustrated.

In FIG. 3B, the equivalent circuit by which the induction currents v1 and v2 from the induction coils 112 and 122 wound in opposite directions cancel each other, thus producing a differential current δv is shown by the dotted arrows. Thus, the circuits shown in FIG. 3A and FIG. 3B are substantially equivalent to each other.

The induction coils 112 and 122 are connected to an amplifier 22 in the signal processor 20.

Since the coils of the sensor 11 have a structure similar to the coils of the sensor 12 when no conductive specimen exists in the electromagnetic fields produced by the exciting coils 111 and 121, the induction currents outputted from the induction coils 112 and 122 are the same or balanced so that an output differential current (or voltage) of the sensor 10 is kept at zero (0) that is, the output currents from the induction coils 112 and 122 connected in opposite phase relationship cancel each other.

However, when a conductive specimen is placed in either of the electromagnetic fields produced by the exciting coils 111 and 121, the output currents from the induction coils 112 and 122 become unbalanced to derive a significant differential value.

That is to say, the exciting coils 111 and 121 produce the electromagnetic fields with the application of an alternating current from an oscillator 21 in the signal processor 20. The induction coils 112 and 122 are exposed to the electromagnetic fields produced by the exciting coils 111 and 121, thus inducing induction currents, respectively. The induction currents outputted from the induction coils 112 and 122 are merged in opposite phase so that the induction currents compensate each other, thus deriving the differential signal between the induction currents. The differential signal is fed to the signal processor 20 through signal lines 13.

In addition to the oscillator 21 capable of applying the alternating current to the sensor unit 10 and adjusting the frequency of the alternating current, and the amplifier 22 for amplifying the differential signal fed from the sensor 10 through the signal lines 13, the signal processor 20 further comprises a phase/amplitude detection and composition unit 23 for determining the phase and amplitude from the differential signal amplified by the amplifier 22 to obtain a composite waveform signal composed of the phase and amplitude, a switching unit 24 including switches and selectors which are handled to perform resetting of the whole processing, switching of output information data (phase and/or amplitude, and composite waveform signal), addressing of output data, and setting of the alternating current from the oscillator 21 to the prescribed frequency within a predetermined frequency range, and an output unit 25 including a microcomputer, an interface circuit (I/F) and an analog-to-digital (A/D) converter for converting the output information data fed from the phase/amplitude detection and composition unit 23 to digital signals.

The signal processor 20 has a signal line 26 through which a signal synchronous with the alternating current generated by the oscillator 21 is fed to the phase/amplitude detection and composition unit 23, a signal line 27 through which a signal for switching the output signal representing the phase and amplitude is fed to the unit 23, and a signal line 29 through which a level signal determined by the switching unit 24 is fed to the oscillator 22.

According to the electromagnetic-induction type inspection device having the aforementioned structure, various conditions of a given test specimen can be recognized on the basis of the phase and amplitude components of the induction current. Prior to the measurement of the test specimen, a standard specimen having no defect is previously tested with this inspection device in order to determine reference characteristic data over a prescribed frequency range and the phase and amplitude inherent in the standard specimen. By analyzing the output data obtained as the result of subjecting the given test specimen to the electromagnetic induction inspection with the aforenoted inspection device of this invention in comparison with the predetermined reference characteristic data, various conditions such as the state, size and location of the internal defects deep within the test specimen can be recognized accurately.

Figure 4:
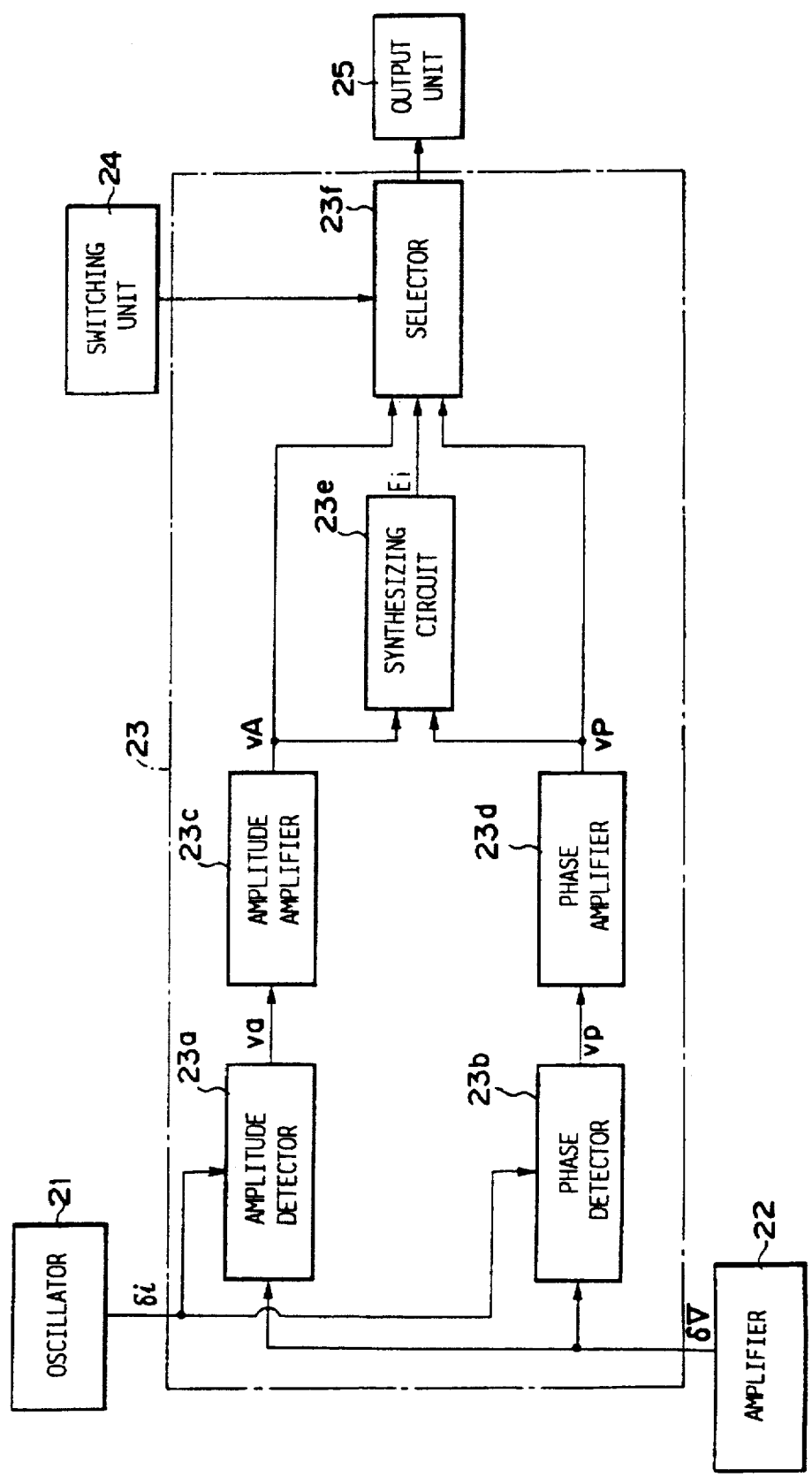
FIG. 4 is a block diagram of a phase/amplitude detection and composition unit in the inspection device of this invention.

As shown in FIG. 4, the aforementioned phase/amplitude detection and composition unit 23 includes an amplitude detector 23a for synchronously rectifying the information signal δv fed from the amplifier 22 with the synchronous signal δi fed from the oscillator 21 to obtain an amplitude signal υa, a phase detector 23b for detecting the phase signal υp from the information signal having an adequate level automatically adjusted by the amplifier 22, circuits 23c and 23d for amplifying the amplitude signal υa from the amplitude detector 23a and the phase signal υp from the phase detector 23b, respectively, into signals υA and υP, a circuit 23e for synthesizing the amplitude signal υA and the phase signal υP to derive a composite signal Ei, and a selector 23f for selectively outputting at least one of the composite signal Ei from the synthesizing circuit 23e, the amplitude signal υA from the amplifying circuit 23c, and the phase signal υP from the amplifying circuit 23d in response to a switching command from the switching unit 24.

Next, the operation of the aforenoted electromagnetic-induction type inspection device will be described.

The oscillator 21 applies the alternating current (i) to the induction sensor unit 10 to excite the exciting coil 111 of the first sensor 11 and the exciting coil 121 of the second sensor 12, and simultaneously, feeds the synchronous signal δi synchronously with the alternating current to the phase/amplitude detection and composition unit 23 through the signal line 26.

In the case of placing a test specimen in one of the alternating electromagnetic fields produced by the first and second sensors 11 and 12, the induction currents induced by the induction coils 112 and 122 are unbalanced to bring about a differential current δv. This differential current δv is given as a detected signal to the signal processor 20 via the signal lines 13 (FIG. 3).

Although, the electric current is described herein as the detected signal for the convenience of description, the measurement according to this invention may be of course fulfilled by measuring the electric voltage or electric power of the detected signal δv.

The detected signal δv given to the signal processor 20 is preliminarily amplified by the amplifier 22 and fed to both the amplitude detector 23a and the phase detector 23b of the phase/amplitude detection and composition unit 23. The respective detected signals δv in the amplitude detector 23a and the phase detector 23b of the phase/amplitude detection and composition unit 23 are synchronously rectified with the synchronous signal δi fed from the oscillator 21 to derive the amplitude component υa or phase component υp of the detected signal δv. The sensitivity of the amplitude or phase component depends on the frequency of the alternating current applied to the exciting coils, which is adjusted by the oscillator 20. Thus, the phase of the detected signal δv changes with the frequency controlled by the switching unit 24.

The lower the frequency generated by the oscillator 21 is, the deeper the magnetic flux spreads into the conductive specimen. Therefore, it is desirable to lower the frequency of the exciting current in finding an internal defect in the test specimen.

The relationship among the frequency, magnetic permeability and specific resistance of the alternating current generated by the oscillator will be described hereinafter.

Assume that the alternating current (i) is given from the oscillator 21 to the exciting coils 111 and 121 of the induction sensor unit 10, the mutual inductance (M) exists between the exciting coil 111 and induction coil 112 and between the exciting coil 121 and induction coil 122, and the complex magnetization rates of the standard specimen (Sa) having no defect and the test specimen (Sb) having an internal defect are ($\mu a+j\rho a$) and ($\mu b+j\rho b$), respectively, where $\mu a$ and $\mu b$ are the magnetic characteristics (magnetic permeability), and $\rho a$ and $\rho b$ are the electrical characteristics (specific resistivity) of the specimens Sa and Sb.

The respective induction voltages "v1" and "v2" induced by the induction coils 112 and 122 are:

$$v1 = j\omega iM(\mu b + j\rho b) = j\omega i\mu_b - \omega iM\rho b \quad \ldots (1)$$

$$v2 = j\omega iM(\mu a + j\rho a) = j\omega iM\mu a - \omega iM\rho a \quad \ldots (2)$$

wherein, $\omega = 2\pi f$ (f: frequency). Since the induction coils 112 and 122 are connected in series in opposite phase relationship so that the induction electromotive voltages v1 and v2 cancel each other, differential voltage δv is:

$$\delta v = v2 - v1 = j\omega iM(\mu a + \mu b) - \omega iM(\rho a - \rho b) \qquad \ldots (3)$$

Here, δv is represented by ωiM(μa-μb) delayed by 90° relative to the current (i) applied to the exciting coils and the components (amplitude υa and phase υp) are independently obtained by the amplitude detector 23a and the phase detector 23b as shown in FIG. 4.

Thus, the standard specimen (Sa) and the test specimen (Sb) are compared in accordance with their magnetic permeabilities (μa; μb) and the specific resistivities (ρa; ρb) obtained in the foregoing manner, consequently revealing the conditions and properties of the test specimen.

Referring to FIG. 4, the amplitude signal υa detected by the amplitude detector 23a and the phase signal υp detected by the phase detector 23b are respectively amplified by the amplifiers 23c and 23d to produce the amplified amplitude signal υA and phase signal υP. The signals υA and υP are given to the synthesizing circuit 23e and the selector 23f. In the synthesizing circuit 23e, the signals υA and υP are synthesized to issue a composite signal Ei to the selector 23f. The selector 23f is controlled in accordance with the switching command given from the switching unit 24 to selectively feed the amplitude signal υA, phase signal υP and/or composite signal Ei to the output unit (I/F) 25.

The output unit (I/F) 25 is also controlled by the switching unit 24 to selectively feed information data including the aforenoted amplitude, phase, and/or composite signals to the display unit 30 to display the information data on a display or the external device 40 including a data recorder.

Next, one example of the experiments which were actually conducted to inspect a test specimen with an internal defect by use of the inspection device of this invention will be described.

Figure 5:
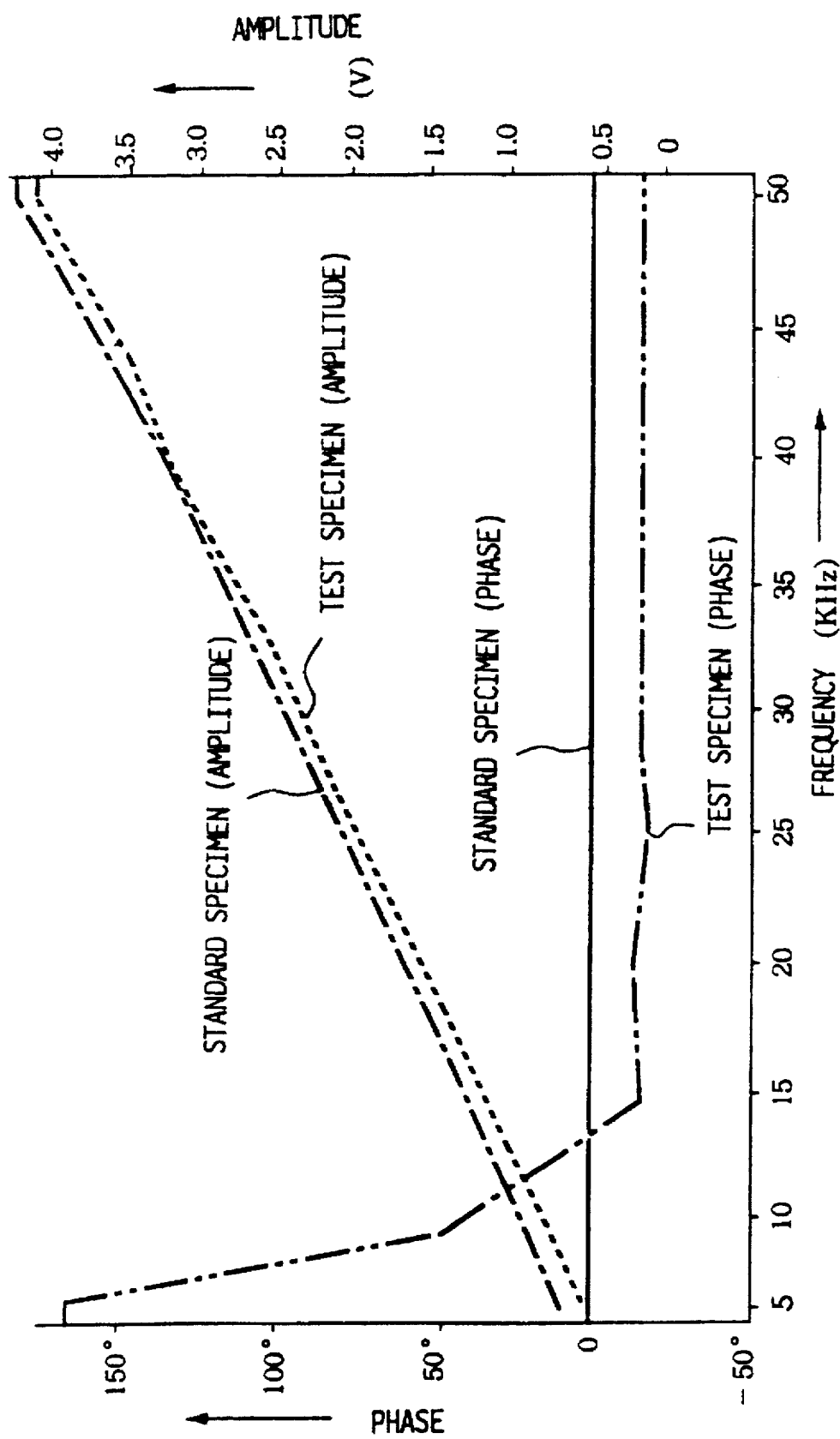
FIG. 5 is a characteristic graph of the amplitude and phase characteristics of the specimens under test.

A characteristic graph depicting the amplitude and phase data resultantly obtained from the experiment is shown in FIG. 5. In this graph, the amplitude and phase characteristics of the test specimen, which vary with the frequency of the alternating current applied to the exciting coils, are illustrated with those of a standard specimen having no defect. In this experiment, as the test specimen, a weld portion generally so-called "nugget" formed by spot welding was used. The frequency values of the alternating current and the detected phase and amplitude values are shown in Table 1 below. The aforesaid exciting current of 5 volts was applied. In the Table 1, the frequency of the applied exciting current shows at intervals of 5 kHz up to 50 kHz as one example.

TABLE 1

| Frequency (kHz) | Standard Specimen | | Test Specimen | |
|---|---|---|---|---|
| | Amplitude (volt) | Phase (°) | Amplitude (volt) | Phase (°) |
| 5 | 0.74 | 0 | 0.65 | 170 |
| 10 | 0.97 | 0 | 0.87 | 50 |
| 15 | 1.35 | 0 | 1.26 | −15 |
| 20 | 1.75 | 0 | 1.62 | −15 |
| 25 | 2.12 | 0 | 2.00 | −20 |
| 30 | 2.50 | 0 | 2.39 | −20 |
| 35 | 2.90 | 0 | 2.80 | −21 |
| 40 | 3.29 | 0 | 3.25 | −22 |
| 45 | 3.72 | 0 | 3.59 | −23 |
| 50 | 4.20 | 0 | 4.20 | −23 |

When no specimen is placed in the electromagnetic field, the induction currents induced by the first sensor 11 and the second sensor 12 are equal to each other to issue a differential current of 0 V.

When the standard specimen (faultless object) having no defect is placed in one of the electromagnetic fields generated by the first and second coils 11 and 12, the amplitude of the induction current changes with the frequency of the applied exciting current as shown in Table 1 and FIG. 5, as the result of which the specific resistivities representing the electrical characteristics of the specimen relative to the frequency of the applied exciting current were obtained.

In the experiment, the phase of the exciting current applied for the standard specimen was set at 0° in order to facilitate comparison to the test specimen having the internal defects (faulty object). As a result, the magnetic permeabilities representing the magnetic characteristics of the specimens could be recognized from the phase data thus obtained.

As shown in FIG. 5, when the test specimen having the internal defects is placed in one of the electromagnetic fields generated by the induction coils, the phase irregularly varies with the variation of frequency, and the amplitude varies dissimilarly to that of the standard specimen. Thus, differential values of the test specimen which are distinguishable from those of the standard specimen could be obtained. This experiment reveals that, with elevating the frequency, the change of differential signal significantly depends on the conditions of the surface of the specimen.

Another experiment made using the inspection device of the invention will be described hereinafter with reference to FIGS. 6A through 6D.

This experiment was carried out by applying an alternating current of the frequency of 20 kHz and 5 V from the oscillator 20 to the exciting coils 11 and 12.

Figure 6A:
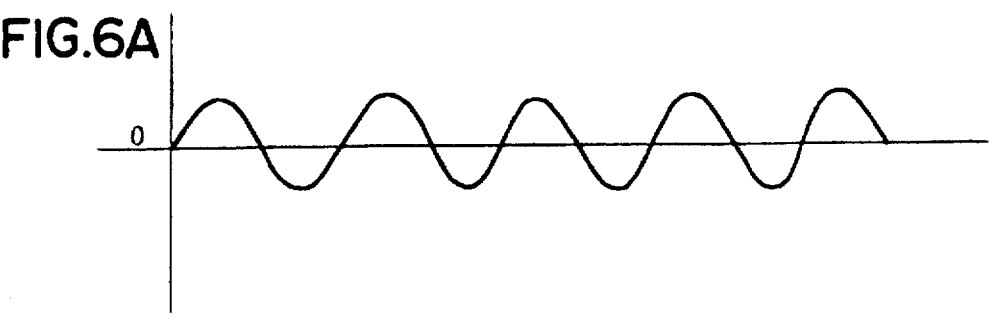
FIG. 6A through FIG. 6D are waveforms of the amplitude and phase data obtained in experiments conducted using the inspection device of this invention.

FIG. 6A shows a reference waveform obtained when no specimen is placed in the electromagnetic fields generated by the exciting coils. This reference waveform expressed by the detected phase and amplitude has the phase of 0° and amplitude of 280 mV.

Figure 6B:
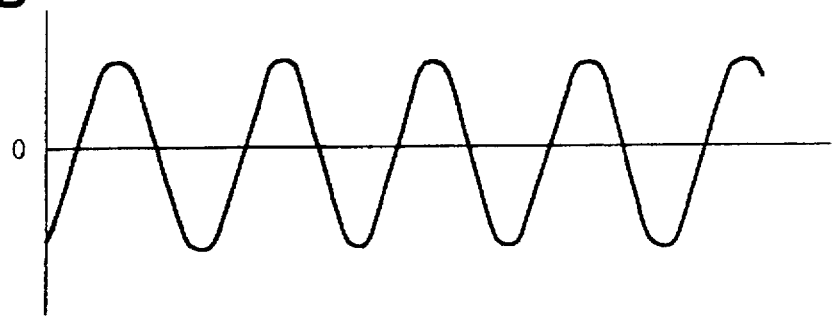

FIG. 6B shows a waveform obtained when a first specimen made of aluminum with 2 mm thickness is placed in one of the electromagnetic fields. This waveform has the phase delayed by 20° and changes to 0.32 V.

Figure 6C:
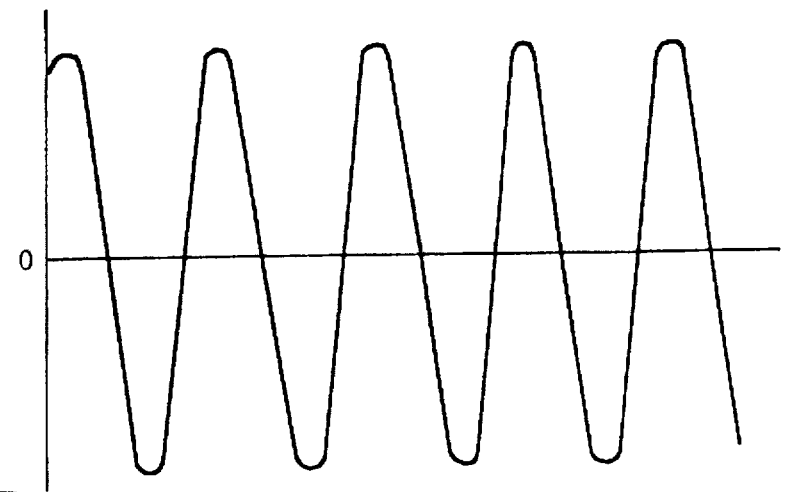

FIG. 6C shows a waveform obtained when a second specimen made of steel (SPCC) with 2 mm thickness is placed in one of the electromagnetic fields. This waveform has the phase delayed by 50° and changes to 0.72 V.

Figure 6D:
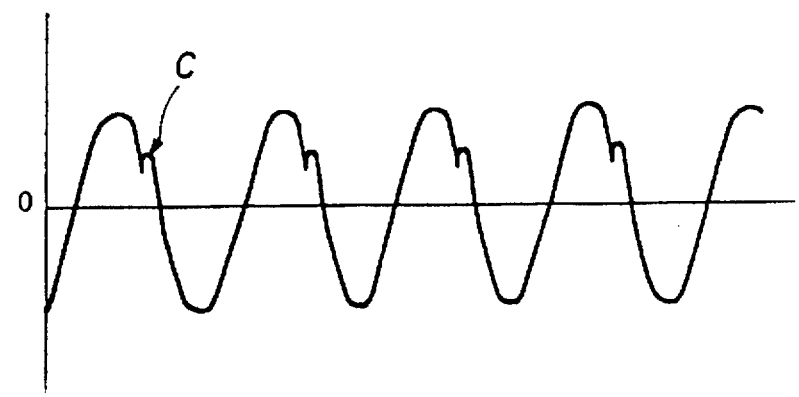

A waveform shown in FIG. 6D was obtained when a third specimen having an internal defect is placed in the electromagnetic field. This third specimen is identical in material and size to the first specimen mentioned above, except for the internal defect embraced therein. Accordingly, the waveform of FIG. 6D is substantially equal to that of FIG. 6B, but contains irregular transitions (deformed portions) C caused by the internal defect.

It will be understood from the aforenoted experimental result that when a given conductive object to be inspected (specimen) has a defect or defects such as a crack and pinhole, an amplitude-phase waveform obtained by placing the object in the electromagnetic field inevitably involves irregularity at specific phase portions. Therefore, by numerically analyzing the data thus obtained in the form of an amplitude-phase waveform by use of the external device 40, the formation such as the size, location and state of the defect can be definitely identified.

Accordingly, by making use of the phenomenon in which the amplitude-phase waveform relative to the frequency of the applied current varies with the solid state properties (specific resistance, magnetic permeability and dielectric constant) of a conductive object to be inspected, it is possible to not merely detect accurately various internal defects or abnormalities including cracks and pinholes in the conductive object such as a welded portion, but also discriminate finely the solid state properties such as carbon content, and quality and density of material of the object by analyzing the phase, amplitude and pattern of the resultant waveform.

The inspection device of this invention is applicable for inspecting all kinds of matter and articles, in particular, mechanical components which are difficult to decompose, e.g. an engine block incorporated in an automobile.

As is apparent from the foregoing description, according to the present invention, since the phenomenon in which the magnetic and electrical characteristics of a given specimen placed in the electromagnetic field generated by the exciting coils vary with the frequency of the exciting current applied to the exciting coils, conditions such as defects, material and dimensions of the specimen can be accurately identified regardless of the quality of material, magnetic permeability, surface conditions, and physical dimensions of the specimen and testing speed and testing arrangement.

Furthermore, since the waveform data resultantly obtained is analyzed in accordance with the detected amplitude and phase, even the location, size and formation of a defect in the given specimen can be readily determined with a high accurate without suffering any disturbance noises.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. An electromagnetic-induction type inspection device comprising:

an oscillator for generating an alternating current adjusted to a specific frequency and for generating a synchronous signal which is synchronized with said alternating current, an electromagnetic induction sensor unit having first and second exciting coils for producing respective first and second electromagnetic fields upon application thereto of said alternating current and first and second induction coils located in said respective first and second electromagnetic fields to induce therein respective first and second induction currents, wherein said induction coils are connected in an opposite phase relationship so as to cause said first and second induction currents to be subtracted from one another to obtain a corresponding differential current having phase and amplitude components, and a signal processor, receiving said differential current and said synchronous signal, and including a phase detection means for synchronously rectifying said differential current with said synchronous signal to detect said phase component of said differential current and to produce a phase signal, an amplitude detection means for synchronously rectifying said differential current with said synchronous signal to detect said amplitude component of said differential current and to produce an amplitude signal, synthesizing means for synthesizing said phase end amplitude signals to produce a composite signal indicative of a composite of said phase and amplitude components, and a selector means for selectively outputting one of said phase, amplitude and composite signals, wherein said differential current varies with conditions of a specimen placed in one of said first and second electromagnetic fields, and wherein said one of said phase, amplitude and composite signals is indicative of at least one condition of the specimen.

2. An inspection device according to claim 1, wherein said first and second induction coils are wound in the same direction and connected to each other so that the first and second induction currents flow in opposite directions to produce said differential current.

3. An inspection device according to claim 1, wherein said first and second induction coils are wound in opposite directions and connected to each other so that the first and second induction currents flow in opposite directions to produce said differential current.

4. An inspection device according to claim 1, wherein said signal processor includes an amplifier for amplifying said differential current.

5. An inspection device according to claim 1, further comprising a display unit, and wherein said composite signal is output as a waveform displayed on said display unit.

6. An inspection device according to claim 1, further comprising means for varying said specific frequency of said alternating current from said oscillator to vary the phase and amplitude components of said composite signal from said signal processor.

* * * * *